United States Patent
Fazekas De St Groth

(10) Patent No.: US 12,061,190 B2
(45) Date of Patent: Aug. 13, 2024

(54) PREDICTING RESPONSES TO IMMUNOTHERAPY

(71) Applicant: ImmuneSignatures Pty Ltd, Concord West (AU)

(72) Inventor: Barbara Fazekas De St Groth, New South Wales (AU)

(73) Assignee: Immunesignatures Pty LTD, Concord West (AU)

( * ) Notice: Subject to any disclaimer, the term of this patent is extended or adjusted under 35 U.S.C. 154(b) by 100 days.

(21) Appl. No.: 16/646,483

(22) PCT Filed: Sep. 12, 2018

(86) PCT No.: PCT/AU2018/050988
§ 371 (c)(1),
(2) Date: Mar. 11, 2020

(87) PCT Pub. No.: WO2019/051542
PCT Pub. Date: Mar. 21, 2019

(65) Prior Publication Data
US 2020/0271641 A1    Aug. 27, 2020

(30) Foreign Application Priority Data

Sep. 12, 2017  (AU) .............................. 2017903703

(51) Int. Cl.
*G01N 33/50* (2006.01)
*C07K 16/28* (2006.01)

(52) U.S. Cl.
CPC ..... *G01N 33/5091* (2013.01); *C07K 16/2818* (2013.01); *G01N 33/5094* (2013.01); *G01N 2800/52* (2013.01)

(58) Field of Classification Search
CPC ......... G01N 33/5094; G01N 33/56972; G01N 2800/52; G01N 33/5091
USPC .................................................. 435/501, 536
See application file for complete search history.

(56) References Cited

U.S. PATENT DOCUMENTS

2009/0311214 A1* 12/2009 Mann ...................... A61P 29/00
424/85.2
2016/0123964 A1* 5/2016 Tumeh ................ C07K 16/2818
435/7.1
2017/0168054 A1  6/2017 Balko et al.

FOREIGN PATENT DOCUMENTS

WO  WO2017/053250       3/2017
WO  WO-2018/136784 A1   7/2018
WO  WO-2018/147291 A1   8/2018

OTHER PUBLICATIONS

Daud et al. (J. Clin. Invest., 126(9):3447-3452, 2016).*
Martens et al. (Clin. Cancer Res., 22(12):2908-2918, Jun. 2016).*
Xie et al., Single Cell Biol, 2023, 12(2): No. 1000057:1-3.*
Lesterhuis et al., Nature Reviews, 2017, 16:264-272.*
Bendall et al., Single-Cell Mass Cytometry of Differential Immune and Drug Responses Across a Human Hematopoietic Continuum, *Science*, 332:687-96 (2011).
Daud et al., Tumor immune profiling predicts response to anti-PD-1 therapy in human melanoma, *J. of Clin. Invest.*, 126:3447-52 (2016).
Davids et al., Ipilimumab for Patients with Relapse after Allogeneic Transplantation, New England Journal of Medicine, 375:43-153 (2016).
Krieg et al., High-dimensional single-cell analysis predicts response to anti-PD-1 immunotherapy, *Nature Medicine*, 24:144-53 (2018).
Martens et al., Baseline Peripheral Blood Biomarkers Associated with Clinical Outcome of Advanced Melanoma Patients Treated with Ipilimumab, *Clinical Cancer Research*, 22:2908-918 (2016).
Subrahmanyam et al ., Distinct predictive biomarker canidtes for response to anti-CTLA-4 and anti-PD-1 immunotherapy in melanoma patients, *J. Immuno. Ther.*, 6(18):1-14 (2018).
Tallerico et al., IL-15, TIM-3 and NK cells subsets predict responsiveness to anti-CTLA-4 treatment in melanoma patients, *Oncolmmunology*, 6(e1261242): 1-12 (2017).
Tietze et al., The proportion of circulating CD45RO+CD8+ memory T cells is correlated with clinical response in melanoma patients treated with ipilimumab, *Euro. J. of Can.*, 75:268-79 (2017).
Wei et al., Distinct Cellular Mechanisms Underlie Anti-CTLA-4 and Anti-PD-1 Checkpoint Blockade, *Cell*, 170:1120-33 (2017).
International Search Report and Written Opinion, PCT/AU2018/050988, dated Nov. 22, 2018.
Ji et al., An immune-active tumor microenvironment favors clinical response to ipilimumab, *Cancer Immunol. Immunother.*, 61:1019-1031 (2012).
Spitzer et al., Mass Cytometry: Single Cells, Many Features, *Cell.*, 165:780-91 (2016).
Therasse et al., New guidelines to evaluate the response to treatment in solid tumors, *J. National Cancer Institute.*, 92:205-16(2000).

* cited by examiner

*Primary Examiner* — Hong Sang
(74) *Attorney, Agent, or Firm* — MARSHALL, GERSTEIN & BORUN LLP

(57) ABSTRACT

The invention relates to methods for determining the likelihood of the formation of a clinical response in an individual to therapy with an immunomodulatory agent for treatment of a disease or condition of the individual.

17 Claims, 8 Drawing Sheets

Figure 6

| Triplet number | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| CD45RO-CCR7-naïve of CD4+ | | | | | x | | | | | x | | | | |
| FoxP3+CD25+CD127loTreg of live | | | | | | | x | | | | | | | |
| CD45RO+memory Treg of live | | x | | | | | | | x | | x | | | x |
| CD45RO-CCR7+naïve CD4+Tcon of live | | | x | | | | | | | | | | x | |
| CD45RO+CCR7+central memory CD4+Tcon of live | | | | | | | | | | | | | x | |
| Integrin Beta7+ of CD45RO+TconCD4+ | x | x | | | | | | | | | | x | x | x |
| CCR6+ of CD45RO+Tcon CD4+ | x | | x | x | x | x | x | x | | x | | x | | |
| CD45RO-naïve CD8+ of live | | | | x | | x | | x | | | x | x | | |
| CD45RO-CCR7+naïve CD8+ of live | | | x | x | | x | | x | x | | | | | |
| CD45RO+memory of CD8+ | | x | | | | x | | x | | x | | | | x |
| CD56+ NK cells of CD3-CD20- | | | | | x | | | | | x | | | | |
| CD14+CD16-Classical Monocytes of live | x | | | | | | | | | | | | | |

PREDICTING RESPONSES TO IMMUNOTHERAPY

CROSS-REFERENCE TO RELATED APPLICATIONS

This is the U.S. national phase of International Application No. PCT/AU2018/050988, filed Sep. 12, 2018, which claims the benefit of Australian Patent Application No. 2017903703, filed Sep. 12, 2017, which are incorporated by reference in their entirety.

FIELD OF THE INVENTION

The invention relates to immunomodulatory agents such as check-point inhibitors for the treatment of cancer and related diseases and conditions, to treatment of cancer and related conditions with same, and to flow cytometry, cell sorting and related techniques.

BACKGROUND OF THE INVENTION

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

The introduction of immunomodulatory agents, including the "check-point inhibitors", has brought the immunotherapy of cancer into mainstream clinical practice for the first time. However these therapies are currently ineffective in a significant proportion of patients, can cause significant side effects, and are very costly. There is an urgent unmet need for new methods of predicting which patients are likely to respond, so as to reduce the burden of side effects (and cost) in non-responders.

SUMMARY OF THE INVENTION

The invention seeks to address one or more of the above mentioned problems or limitations and in one embodiment provides a method for determining the likelihood of the formation of a clinical response in an individual to therapy with an immunomodulatory agent for treatment of a disease or condition of the individual, including:
  (i) providing a positive response control derived from a positive responder in the form of an individual who has formed the clinical response to therapy with the immunomodulatory agent for treatment of the disease or condition, the positive response control describing the distribution of cells of a sample of the positive responder within a series of classes, the distribution according to the expression by each cell of the sample of a group of biomarkers so that cells having the same expression of each biomarker of the group are classified in the same class;
  (ii) determining the distribution of cells of a test sample within the series of classes of the positive response control, the test sample in the form of a sample of cells from the individual for whom the likelihood of formation of a clinical response is to be determined; and
  (iii) determining whether the distribution of the cells of the test sample within the series of classes of the positive response control is the same as the distribution of cells described by the positive response control;
  whereby a higher likelihood of formation of a clinical response is determined where the distribution of the cells of the test sample within the series of classes of the positive response control is the same as the distribution of cells described by the positive response control
  and
  whereby a lower likelihood of formation of a clinical response is determined where the distribution of the cells of the test sample within the series of classes of the positive response control is not the same as the distribution of cells described by the positive response control.

In another embodiment there is provided a method for determining the likelihood of the formation of a clinical response in an individual to therapy with a checkpoint inhibitor for treatment of cancer of the individual, including:
  (i) providing a positive response control derived from a positive responder in the form of an individual who has formed the clinical response to therapy with the checkpoint inhibitor for treatment of the cancer, the positive response control describing the distribution of cells of a sample of the positive responder within a series of classes, the distribution according to the expression by each cell of the sample of a group of biomarkers including chemokine receptors and integrins so that cells having the same expression of each biomarker of the group are classified in the same class;
  (ii) determining the distribution of cells of a test sample within the series of classes of the positive response control, the test sample in the form of a sample of cells from the individual for whom the likelihood of formation of a clinical response is to be determined; and
  (iii) determining whether the distribution of the cells of the test sample within the series of classes of the positive response control is the same as the distribution of cells described by the positive response control;
  whereby a higher likelihood of formation of a clinical response is determined where the distribution of the cells of the test sample within the series of classes of the positive response control is the same as the distribution of cells described by the positive response control
  and
  whereby a lower likelihood of formation of a clinical response is determined where the distribution of the cells of the test sample within the series of classes of the positive response control is not the same as the distribution of cells described by the positive response control.

Preferably the checkpoint inhibitor is an anti-PD-1 antibody.

In another embodiment there is provided a method for determining the likelihood of the formation of a clinical response in an individual to therapy with a checkpoint inhibitor for treatment of cancer of the individual, including:
  (i) providing a positive response control derived from a positive responder in the form of an individual who has formed the clinical response to therapy with the checkpoint inhibitor for treatment of the cancer, the positive response control describing the distribution of cells of a sample of the positive responder within a series of classes, the distribution according to the expression by each cell of the sample of a group of biomarkers so that cells having the same expression of each biomarker of the group are classified in the same class;

(ii) determining the distribution of cells of a test sample within the series of classes of the positive response control, the test sample in the form of a sample of cells from the individual for whom the likelihood of formation of a clinical response is to be determined; and
(iii) determining whether the distribution of the cells of the test sample within the series of classes of the positive response control is the same as the distribution of cells described by the positive response control;
whereby a higher likelihood of formation of a clinical response is determined where the distribution of the cells of the test sample within the series of classes of the positive response control is the same as the distribution of cells described by the positive response control
and
whereby a lower likelihood of formation of a clinical response is determined where the distribution of the cells of the test sample within the series of classes of the positive response control is not the same as the distribution of cells described by the positive response control
and
(iv) administering the checkpoint inhibitor to the individual for whom the likelihood of formation of a clinical response is to be determined where a higher likelihood of formation of a clinical response is determined for the individual.

In another embodiment there is provided a method for identifying a positive response control in the form of a cell distribution profile that is predictive of an individual responding to therapy with a check point inhibitor including:
(i) providing a responder cell sample in the form of cells of an individual who has responded to immune check point inhibitor therapy;
(ii) providing a non responder cell sample in the form of cells of an individual who has not responded to immune check point inhibitor therapy;
(iii) applying a cell distribution analysis to the responder cell sample whereby the cells in the responder cell sample are distributed within a series of classes according to the expression by each cell of a group of biomarkers so that cells having the same expression of each biomarker of the group are classified in the same class, thereby forming a responder cell distribution profile;
(iv) applying the cell distribution analysis to the non responder cell sample, thereby forming a non responder cell distribution profile;
(v) identifying a distribution of cells in the responder cell distribution profile that is not seen in the non responder cell distribution profile;
wherein a distribution of cells in the responder cell distribution profile that is not seen in the non responder cell distribution profile is identified as a positive response control.

Typically the above described methods are performed in vitro.

In another embodiment there is provided a method for treatment of cancer of an individual who has been determined to have a higher likelihood of the formation of a clinical response to therapy with a checkpoint inhibitor, comprising administering an effective amount of the checkpoint inhibitor, wherein the individual has been determined to have a likelihood of the formation of a clinical response to therapy with a checkpoint inhibitor by a method including:

(i) providing a positive response control derived from a positive responder in the form of an individual who has formed the clinical response to therapy with the checkpoint inhibitor for treatment of the cancer, the positive response control describing the distribution of cells of a sample of the positive responder within a series of classes, the distribution according to the expression by each cell of the sample of a group of biomarkers including chemokine receptors and integrins so that cells having the same expression of each biomarker of the group are classified in the same class;
(ii) determining the distribution of cells of a test sample within the series of classes of the positive response control, the test sample in the form of a sample of cells from the individual for whom the likelihood of formation of a clinical response is to be determined; and
(iii) determining whether the distribution of the cells of the test sample within the series of classes of the positive response control is the same as the distribution of cells described by the positive response control;
whereby a higher likelihood of formation of a clinical response is determined where the distribution of the cells of the test sample within the series of classes of the positive response control is the same as the distribution of cells described by the positive response control
and
whereby a lower likelihood of formation of a clinical response is determined where the distribution of the cells of the test sample within the series of classes of the positive response control is not the same as the distribution of cells described by the positive response control.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 6. Triplets of parameters that assigned responders and non-responders to the correct groups in a machine learning analysis of the advanced melanoma dataset illustrated in FIG. 1.

DETAILED DESCRIPTION OF THE EMBODIMENTS

Figure 1:
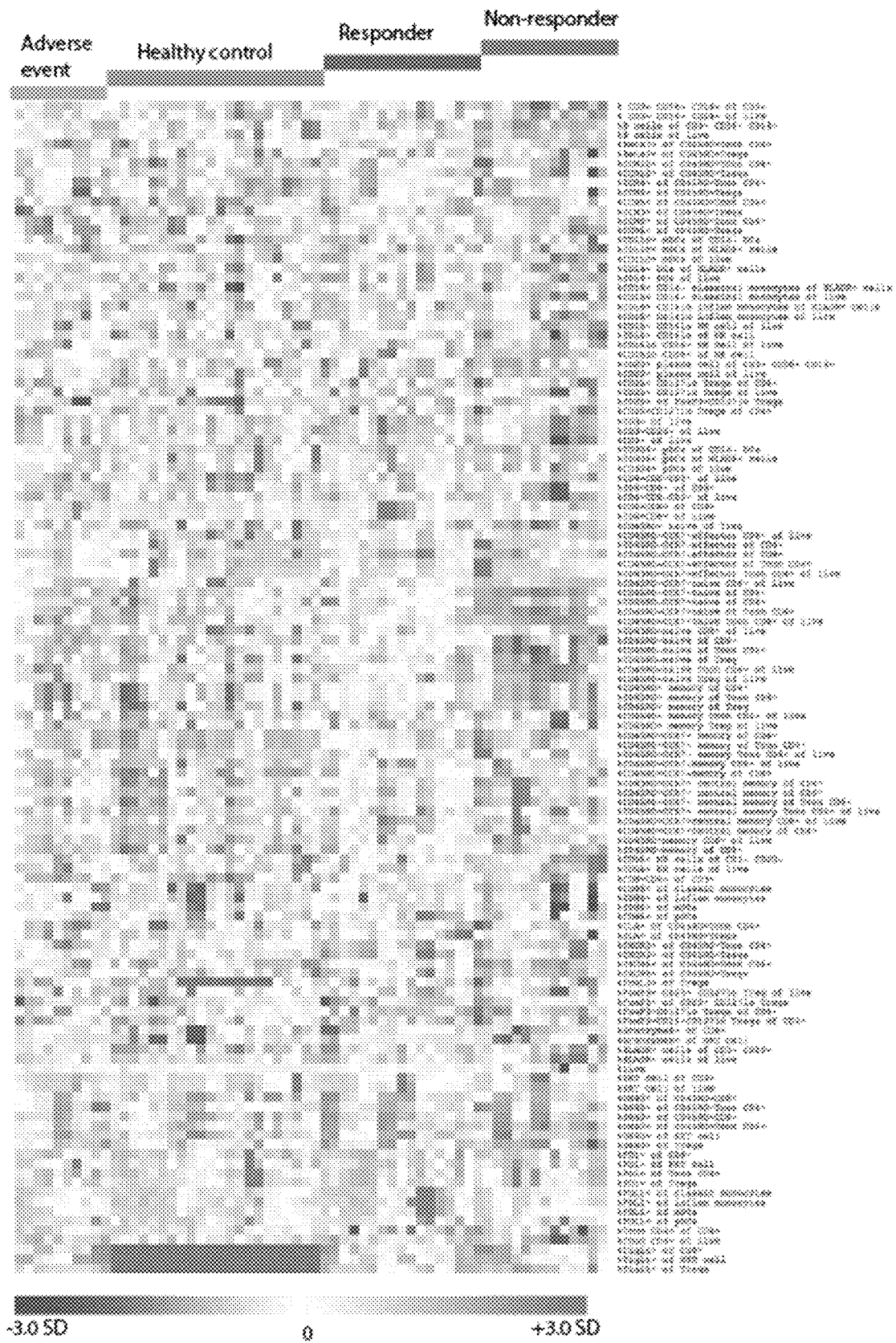
FIG. 1. Heat map of the dataset generated from 40-parameter mass cytometric analysis of PBMCs from advanced melanoma patients and controls. Columns show samples from each individual: paired pre- and post-therapy samples from each patient (7 responders, 6 non-responders and 5 patients who discontinued therapy due to adverse events). Age- and sex-matched controls provided a single sample. Rows represent measured parameters (% cells in each subpopulation, row normalized to show SD from mean as indicated by the colour bar at bottom).

In one embodiment, there is provided a method for determining the likelihood of the formation of a clinical response in an individual to therapy with an immunomodulatory agent for treatment of a disease or condition of the individual. The method includes the following steps:

(i) providing a positive response control derived from a positive responder in the form of an individual who has formed a clinical response to therapy with the immunomodulatory agent for treatment of the disease or condition, the positive response control describing the distribution of cells of a sample of the positive responder within a series of classes, the distribution according to the expression by each cell of the sample of a group of biomarkers so that cells having the same expression of each biomarker of the group are classified in the same class;

(ii) determining the distribution of cells of a test sample within the series of classes of the positive response control, the test sample in the form of a sample of cells from the individual for whom the likelihood of formation of a clinical response is to be determined; and (iii) determining whether the distribution of the cells of the test sample within the series of classes of the positive response control is the same as the distribution of cells described by the positive response control.

According to the method, a higher likelihood of formation of a clinical response is determined where the distribution of the cells of the test sample within the series of classes of the positive response control is the same as the distribution of cells described by the positive response control. A lower likelihood of formation of a clinical response is determined where the distribution of the cells of the test sample within the series of classes of the positive response control is not the same as the distribution of cells described by the positive response control.

The phrase "same as the distribution" in the context of "determining whether the distribution of the cells of the test sample within the series of classes of the positive response control is the same as the distribution of cells described by the positive response control" and grammatical variants thereof will be generally understood as referring to a level of similarity or identity between the test sample and the positive response control. Preferably the distribution is the same across at least the majority of classes of the positive response control. In some embodiments, there may be some difference in distribution in a minority of classes of the positive response control.

Types of Clinical Responses

The method may be used to predict or determine likelihood of a complete response or partial response, or whether a response is likely to be a complete response or a partial response. As generally understood, a 'complete response' to therapy is generally understood as meaning the disappearance of all detectable signs of cancer in response to treatment. A 'partial response' is generally understood as meaning a decrease in tumour load in an individual, for example in terms of tumour number, size and growth rate. A partial response may increase the time to disease progression.

In the embodiments of the invention described herein, a clinical response, such as a complete response or a partial response may be defined by RECIST 1.0 criteria (Therasse P, et al.) 2000 *J. Natl Cancer Inst* 92:2015-16 as described below.

RECIST 1.0 Criteria

A. Definition of Measurable and Non-measurable Disease

Measurable disease: The presence of at least one measurable lesion.

Measurable lesion: Lesions that can be accurately measured in at least one dimension, with the longest diameter (LD) being:

≥20 mm with conventional techniques (medical photograph [skin or oral lesion], palpation, plain X-ray, CT, or MRI),

OR

≥10 mm with spiral CT scan.

Non-measurable lesion: All other lesions including lesions too small to be considered measurable (longest diameter <20 mm with conventional techniques or <10 mm with spiral CT scan) including bone lesions, leptomeningeal disease, ascites, pleural or pericardial effusions, lymphangitis cutis/pulmonis, abdominal masses not confirmed and followed by imaging techniques, cystic lesions, or disease documented by indirect evidence only (e.g., by lab values).

B. Methods of Measurement

Conventional CT and MRI: Minimum sized lesion should be twice the reconstruction interval. The minimum size of a baseline lesion may be 20 mm, provided the images are reconstructed contiguously at a minimum of 10 mm. MRI is preferred, and when used, lesions must be measured in the same anatomic plane by use of the same imaging sequences on subsequent examinations. Whenever possible, the same scanner should be used.

Spiral CT: Minimum size of a baseline lesion may be 10 mm, provided the images are reconstructed contiguously at 5 mm intervals. This specification applies to the tumors of the chest, abdomen, and pelvis.

Chest X-ray: Lesions on chest X-ray are acceptable as measurable lesions when they are clearly defined and surrounded by aerated lung. However, MRI is preferable.

Clinical Examination: Clinically detected lesions will only be considered measurable by RECIST criteria when they are superficial (e.g., skin nodules and palpable lymph nodes). In the case of skin lesions, documentation by color photography—including a ruler and patient study number in the field of view to estimate the size of the lesion—is required.

C. Baseline Documentation of Target and Non-Target Lesions

All measurable lesions up to a maximum of five lesions per organ and ten lesions in total, representative of all involved organs, should be identified as target lesions and recorded and measured at baseline.

Target lesions should be selected on the basis of their size (lesions with the LD) and their suitability for accurate repeated measurements (either clinically or by imaging techniques).

A sum of the LD for all target lesions will be calculated and reported as the baseline sum LD. The baseline sum LD will be used as a reference by which to characterize the objective tumor response.

All other lesions (or sites of disease) should be identified as non-target lesions and should also be recorded at baseline. Measurements of these lesions are not required, but the presence or absence of each should be noted throughout follow-up.

Documentation of indicator lesion(s) should include date of assessment, description of lesion site, dimensions, and type of diagnostic study used to follow lesion(s).

All measurements should be taken and recorded in metric notation, using a ruler or callipers.

D. Response Criteria

Disease assessments are to be performed every 6 weeks after initiating treatment. However, subjects experiencing a partial or complete response must have a confirmatory disease assessment at least 28 days later. Assessment should be performed as close to 28 days later (as scheduling allows), but no earlier than 28 days.

Definitions for assessment of response for target lesion(s) are as follows:

Evaluation of Target Lesions

Complete Response (CR)—disappearance of all target lesions.

Partial Response (PR)—at least a 30% decrease in the sum of the LD of target lesions, taking as a reference, the baseline sum LD.

Stable Disease (SD)—neither sufficient shrinkage to qualify for PR nor sufficient increase to qualify for progressive disease (PD), taking as a reference, the smallest sum LD since the treatment started. Lesions, taking as a reference, the smallest sum LD recorded since the treatment started or the appearance of one or more new lesions.

E. Evaluation of Non-Target Lesions

Definitions of the criteria used to determine the objective tumor response for non-target lesions are as follows:

Complete Response—the disappearance of all non-target lesions.

Incomplete Response/Stable Disease—the persistence of one or more non-target lesion(s).

Progressive Disease—the appearance of one or more new lesions and/or unequivocal progression of existing non-target lesions.

F. Evaluation of Overall Response for RECIST-Based Response

The overall response is the best response recorded from the start of the treatment until disease progression/recurrence is documented. In general, the subject's best response assignment will depend on the achievement of both measurement and confirmation criteria.

The following table presents the evaluation of best overall response for all possible combinations of tumor responses in target and non-target lesions with or without the appearance of new lesions.

| Target Lesion | Non-Target Lesion | New Lesion | Overall response |
| --- | --- | --- | --- |
| CR | CR | No | CR |
| CR | Incomplete response/(SD) | No | PR |
| PR | Non-PD | No | PR |
| SD | Non-PD | No | SD |
| PD | Any | Yes or No | PD |
| Any | PD | Yes of No | PD |
| Any | Any | Yes | PD |

Note: Subjects with a global deterioration of health status requiring discontinuation of treatment without objective evidence of disease progression at that time should be classified as having "symptomatic deterioration". Every effort should be made to document the objective progression even after discontinuation of treatment.

In some circumstances, it may be difficult to distinguish residual disease from normal tissue. When the evaluation of complete response depends on this determination, it is recommended that the residual lesion be investigated (fine needle aspirate/biopsy) to confirm the complete response status.

G. Confirmation Criteria

To be assigned a status of PR or CR, a confirmatory disease assessment should be performed no less than 28 days after the criteria for response are first met.

To be assigned a status of SD, follow-up measurements must have met the SD criteria at least once after study entry at a minimum interval of 12 weeks.

In a preferred embodiment, the method is for determining the likelihood of the formation of a complete response in an individual to therapy with an immunomodulatory agent for treatment of a disease or condition of the individual.

Where the need is to determine likelihood of a complete response, the positive response control is derived from a positive responder or a cohort of positive responders that has formed a complete response. In contrast, where the need is to determine likelihood of a partial response, the positive response control is derived from a positive responder or a cohort of positive responders that has formed a partial response.

Preparation of Positive Response Control

The invention may include the further step of assessing one or more organs or tissues of an individual who has received the immunomodulatory agent, to determine the regression of a tumour in the individual, and therefore to determine whether that individual is suitable for providing a positive response control. For example, where the method is for predicting likelihood of a complete response, the step includes an assessment of whether the candidate individual for providing a positive response control has made a complete or partial response or whether there has been any response at all. In one embodiment the step utilises radiological imaging to determine the location and volume for each of the plurality of tumor lesions in the subject after treatment with the immunomodulatory agent. For example, this can involve three-dimensional radiological images of the subject registering geographic locations of each of the plurality of tumor lesions. Non-limiting examples of radiological images that can be used to determine location and/or volume of a tumor lesion include positron emission tomography (PET) scans, x-ray computerized tomography (CT), magnetic resonance imaging (MRI), nuclear magnetic resonance imaging (NMRI), magnetic resonance tomography (MRT), or a combination thereof.

The positive response control may be derived from a single individual. However, in some embodiments it is preferred that the positive response control is derived from a cohort of positive responders.

As described herein, where a cohort or plurality of positive responders is used to derive a positive response control, the control is based on distribution data arising from an individual assessment of each of the positive responder samples selected for derivation of the positive response control. Thus each responder sample is assessed to determine a cell distribution profile specific to each sample. These cell distribution profiles are then compiled to form the positive response control.

The compilation may enable the identification of cell populations that are predominantly associated with a clinical response to therapy in the majority of responders. The relevant statistical methods are understood by the skilled worker and described further herein.

In one embodiment, the positive response control describes the distribution of cells of a sample of a positive responder prior to therapy, or post therapy, of the positive responder with the immunomodulatory agent. Preferably the positive response control describes the distribution of cells of a positive responder, before the positive responder is subjected to treatment with the immunomodulatory agent leading to the positive response.

As described herein, a purpose of the positive response control is to provide a reference point against which a prediction of the likelihood of another individual forming a clinical response to treatment with the same immunomodulatory agent (i.e. same as used for formation of the positive response control) for, preferably, the same disease or condition (i.e. same as treated in the individual from which the positive response control is derived) is made. The prediction is made on the basis of the comparison between test sample and positive response control. The comparison may be as between the frequency of cells in defined classes or subpopulations of cells of the positive response control and the test sample.

In one embodiment, a positive response control may be identified according to the following steps:
(i) provide a responder cell sample in the form of cells of an individual who has responded to therapy with an immunomodulatory agent
(ii) provide a non responder cell sample in the form of cells of an individual who has not responded to therapy with an immunomodulatory agent
(iii) apply a cell distribution analysis to the responder cell sample whereby the cells in the responder cell sample are distributed within a series of classes according to the expression by each cell of a group of biomarkers so that cells having the same expression of each biomarker of the group are classified in the same class, thereby forming a responder cell distribution profile
(iv) apply the same cell distribution analysis, albeit to the non responder cell sample, thereby forming a non responder cell distribution profile
(v) identify a distribution of cells in the responder cell distribution profile that is not seen in the non responder cell distribution profile, wherein a distribution of cells in the responder cell distribution profile that is not seen in the non responder cell distribution profile is identified as a positive response control.

Typically the responder cell distribution profile is a compilation of cell distribution profiles of different responders. This increases the likelihood that the control contains the cell distributions that are associated with response to therapy in the bulk of individuals who have responded to therapy.

Typically, the plurality of non responder cell samples may be a compilation of cell distribution profiles of different non responders.

The cells may be distributed according to the expression of at least 10 biomarkers, although the number of biomarkers could be 20, 30, 40, 100 or more.

The phrase "same expression" in the context of "cells having the same expression", and grammatical variants thereof will be generally understood as referring to a level of identity or similarity as between the relevant subjects. The level of identity or similarity may be a function of the number of responder cell distribution profiles that form the positive response control. Where a positive response control arises from a compilation of responder cell distribution profiles, it may be expected that "same expression" refers to a lower level of identity as between relevant subjects than might be expected where the positive response control is derived from a single responder cell distribution profile.

In some embodiments the cells may be assessed for the absence of expression of a biomarker, or the presence of expression of a biomarker. In some embodiments the cells may be assessed for a particular level of expression of a biomarker. For example, cells may be expressed for a 'low' level of expression of a biomarker (for example, $CD4^{lo}$) or a 'high' level of expression of a biomarker (for example, $CD4^{hi}$). The meaning of level of biomarker expression referred to as 'hi' or 'lo' is generally well understood by the skilled worker. For example, the meaning of a $CD4^{hi}$ and a $CD4^{lo}$ T cell, or of a $CD127^{hi}$ and a $CD127^{lo}$ T cell is understood by the skilled worker and is routinely determined using standard techniques.

For the purpose of merely exemplifying the method, in one example, cells may be analysed to determine whether they can be distributed within the class $CD25^+CD127^{lo}T_{reg}$. In this example, antibodies specific for CD25, CD127 and various other $T_{reg}$ markers may be utilised. In this example, cells that have $CD25^+CD127^{lo}T_{reg}$ are distributed in this class. Cells that have $CD25^-CD127^{lo}T_{reg}$ or $CD25^+CD127^{hi}T_{reg}$ or $CD25^-CD127^{hi}T_{reg}$ are not distributed into the $CD25^+CD127^{lo}T_{reg}$ class.

Typically the biomarkers are molecules that are characteristically expressed by cells having immune function, including lymphocytes, monocytes, granulocytes and the like.

In one embodiment, the biomarkers may be molecules that are expressed by cells associated with autoimmunity.

In one embodiment the group of biomarkers includes chemokine receptors, and/or integrins. Preferred chemokine receptors include CCR3, CCR4, CCR5, CCR6, CCR7, CXCR3 and CXCR5. Preferred integrins include β7.

In one embodiment, the group of biomarkers includes molecules that are expressed by CD4 T cells or CD8 T cells, preferably CD4 T cells. The CD4 T cells may be Treg, naïve or memory T cells.

In one embodiment, the group of biomarkers includes a CD4 or CD8 T cell marker and at least 9 markers, typically at least 10, 11, 12, 13, 14, 15, 16, 17 or 18 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a CD4 or CD8 T cell marker and at least 19 markers, typically at least 20, 21, 22, 23, 24, 25, 26, 27, or 28 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a CD4 or CD8 T cell marker and at least 29 markers, typically at least 30, 31, 32, 33, 34, 35, 36, 37, or 38 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a CD4 or CD8 Tcell marker and at least 39 markers from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes molecules that are expressed by B cells or plasma cells.

In one embodiment, the group of biomarkers includes a B cell or plasma cell marker and at least 9 markers, typically at least 10, 11, 12, 13, 14, 15, 16, 17 or 18 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a B cell or plasma cell marker and at least 19 markers, typically at least 20, 21, 22, 23, 24, 25, 26, 27, or 28 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a CD4 or CD8 T cell marker and at least 29 markers, typically at least 20, 21, 22, 23, 24, 25, 26, 27, or 28 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a B cell or plasma cell marker and at least 39 markers from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes molecules that are expressed by NK cells.

In one embodiment, the group of biomarkers includes a NK cell marker and at least 9 markers, typically at least 10, 11, 12, 13, 14, 15, 16, 17 or 18 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a NK cell marker and at least 19 markers, typically at least 20, 21, 22, 23, 24, 25, 26, 27, or 28 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a NK cell marker and at least 29 markers, typically at least 20, 21, 22, 23, 24, 25, 26, 27, or 28 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a NK cell marker and at least 39 markers from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes molecules that are expressed by monocytes or dendritic cells.

In one embodiment, the group of biomarkers includes a monocytes or dendritic cell marker and at least 9 markers, typically at least 10, 11, 12, 13, 14, 15, 16, 17 or 18 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a monocytes or dendritic cell marker and at least 19 markers, typically at least 20, 21, 22, 23, 24, 25, 26, 27, or 28 markers, from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a monocyte or dendritic cell marker and at least 29 markers, typically at least 20, 21, 22, 23, 24, 25, 26, 27, or 28 markers, from the group consisting of CD45, CD45RA, CD45RO, CD3, CD4, CD8, CD19, CD20, CD14, CD16, CD11, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the group of biomarkers includes a monocytes or dendritic cell marker and at least 39 markers from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10.

In one embodiment, the positive response control may describe the distribution of cells within a series of at least 10, 20, 30, 40 or 50 classes of cells, preferably 100, preferably 150 preferably 200 classes of cells.

In one embodiment, the cells of the test sample are not assessed for T cell or B cell receptor diversity.

The positive response control may describe the distribution of cells of a positive responder as the number of cells per class as a % of total number of cells. In one embodiment, preferably where the checkpoint inhibitor is an anti-PD-1 antibody, the distribution of cells that is assessed is according to Table 1 below.

TABLE 1

| Cell distribution |
| --- |
| % CD3− CD56− CD14− of CD3− |
| % CD3− CD56− CD14− of live |
| % B cells of CD3− CD56− CD14− |
| % B cells of live |
| % Beta7+ of CD45RO+ Tcon CD4+ |
| % Beta7+ of CD45RO+ Tregs |
| % CCR10+ of CD45RO+ Tcon CD4+ |
| % CCR10+ of CD45RO+ Tregs |
| % CCR4+ of CD45RO+ Tcon CD4+ |
| % CCR4+ of CD45RO+ Tregs |

TABLE 1-continued

| Cell distribution |
| --- |
| % CCR5+ of CD45RO+ Tcon CD4+ |
| % CCR5+ of CD45RO+ Tregs |
| % CCR6+ of CD45RO+ Tcon CD4+ |
| % CCR6+ of CD45RO+ Tregs |
| % CD11c+ mDCs of CD14− DCs |
| % CD11c+ mDCs of HLADR+ cells |
| % CD11c+ mDCs of live |
| % CD14− DCs of HLADR+ cells |
| % CD14− DCs of HLADR+ cells |
| % CD14− DCs of live |
| % CD14+ CD16− classical monocytes of HLADR+ cells |
| % CD14+ CD16− classical monocytes of live |
| % CD16+ CD14lo inflam monocytes of HLADR+ cells |
| % CD16+ CD14lo inflam monocytes of live |
| % CD16+ CD56lo NK cell of live |
| % CD16+ CD56lo of NK cell |
| % CD16lo CD56+ NK cell of live |
| % CD16lo CD56+ of NK cell |
| % CD20+ plasma cell of CD3− CD56− CD14− |
| % CD20+ plasma cell of live |
| % CD25+ CD127lo Tregs of CD4+ |
| % CD25+ CD127lo Tregs of live |
| % CD25+ of FoxP3+ CD127lo Tregs |
| % CD25+ CD127lo Tregs of CD4+ |
| % CD3− of live |
| % CD3− CD20− of live |
| % CD3+ of live |
| % CD304+ pDCs of CD14− DCs |
| % CD304+ pDCs of HLADR+ cells |
| % CD304+ pDCs of live |
| % CD4− CD8+ CD3+ of live |
| % CD4+ CD8− of CD3+ |
| % CD4+ CD8− CD3+ of live |
| % CD4+ CD8+ of CD3+ |
| % CD4+ CD8+ of live |
| % CD45RO− naive of Treg |
| % CD45RO− CCR7− effector CD8+ of live |
| % CD45RO− CCR7− effector of CD4+ |
| % CD45RO− CCR7− effector of CD8+ |
| % CD45RO− CCR7− effector of Tcon CD4+ |
| % CD45RO− CCR7− effector Tcon CD4+ of live |
| % CD45RO− CCR7+ naive CD8+ of live |
| % CD45RO− CCR7+ naive of CD4+ |
| % CD45RO− CCR7+ naive of CD8+ |
| % CD45RO− CCR7+ naive of Tcon CD4+ |
| % CD45RO− CCR7+ naive Tcon CD4+ of live |
| % CD45RO− naive CD8+ of live |
| % CD45RO− naive of CD8+ |
| % CD45RO− naive of Tcon CD4+ |
| % CD45RO− naive Tcon CD4+ of live |
| % CD45RO− naive Treg of live |
| % CD45RO+ memory of CD4+ |
| % CD45RO+ memory of Tcon CD4+ |
| % CD45RO+ memory of Treg |
| % CD45RO+ memory Tcon CD4+ of live |
| % CD45RO+ memory Treg of live |
| % CD45RO+ CCR7− memory of CD4+ |
| % CD45RO+ CCR7− memory of Tcon CD4+ |
| % CD45RO+ CCR7− memory Tcon CD4+ of live |
| % CD45RO+ CCR7− memory CD8+ of live |
| % CD45RO+ CCR7− memory of CD8+ |
| % CD45RO+ CCR7+ central memory of CD4+ |
| % CD45RO+ CCR7+ central memory of CD8+ |
| % CD45RO+ CCR7+ central memory of Tcon CD4+ |
| % CD45RO+ CCR7+ central memory Tcon CD4+ of live |
| % CD45RO+ CCR7+ central memory CD8+ of live |
| % CD45RO+ CCR7+ central memory of CD8+ |
| % CD45RO+ memory CD8+ of live |
| % CD45RO+ memory of CD8+ |
| % CD56+ NK cells of CD3− CD20− |
| % CD56+ NK cells of live |
| % CD8+ CD4− of CD3+ |
| % CD86+ of inflam monocytes |
| % CD86+ of mDCs |
| % CD86+ of pDCs |
| % CLA+ of CD45RO+ Tcon CD4+ |
| % CLA+ of CD45RO+ Tregs |
| % CXCR3+ of CD45RO+ Tcon CD4+ |

TABLE 1-continued

Cell distribution

% CXCR3+ of CD45RO+ Tregs
% CXCR5+ of CD45RO+ Tcon CD4+
% CXCR5+ of CD45RO+ Tregs
% FcRL3+ of Tregs
% FoxP3+ CD25+ CD127lo Treg of live
% FoxP3+ of CD25+ CD127lo Tregs
% FoxP3+ CD127lo Tregs of CD4+
% FoxP3+ CD25+ CD127lo Tregs of CD4+
% GranzymeB+ of CD8+
% GranzymeB+ of NKT cell
% HLADR+ cells of CD3− CD20−
% HLADR+ cells of live
% live
% NKT cell of CD3+
% NKT cell of live
% OX40+ of CD45RO− CD8+
% OX40+ of CD45RO− Tcon CD4+
% OX40+ of CD45RO+ CD8+
% OX40+ of CD45RO+ Tcon CD4+
% OX40+ of NKT cell
% OX40+ of Tregs
% PD1+of CD8+
% PD1+of NKT cell
% PD1+ of Tcon CD4+
% PD1+ of Tregs
% PDL1+ of classic monocytes
% PDL1+ of inflam monocytes
% PDL1+ of mDCs
% PDL1+ of pDCs
% Tcon CD4+ of CD4+
% Tcon CD4+ of live
% Tigit+ of Tregs
% Tigit+ of NKT cell
% Tigit+ of CD8+
% GranzymeB+ of CD8+
% GranzymeB+ of NKT cell
% OX40+ of CD45RO+ Tcon CD4+
% OX40+ of CD45RO− Tcon CD4+
% OX40+ of Tregs
% OX40+ of CD45RO+ CD8+
% OX40+ of CD45RO− CD8+
% CD86+ of classic monocytes
% CD86+ of mDCs
% CD86+ of pDCs
% CD86+ of inflam monocytes
% FcRL3+ of Tregs
% PDL1+ of classic monocytes
% PDL1+ of mDCs
% PDL1+ of pDCs
% PDL1+ of inflam monocytes
% CCR4+ of CD45RO+ Tcon CD4+
% CCR5+ of CD45RO+ Tcon CD4+
% CCR6+ of CD45RO+ Tcon CD4+
% CCR10+ of CD45RO+ Tcon CD4+
% Beta7+ of CD45RO+ Tcon CD4+
% CLA+ of CD45RO+ Tcon CD4+
% CXCR3+ of CD45RO+ Tcon CD4+
% CCR5+ of CD45RO+ Tregs
% CCR6+ of CD45RO+ Tregs
% CCR10+ of CD45RO+ Tregs
% Beta7+ of CD45RO+ Tregs
% CLA+ of CD45RO+ Tregs
% CXCR3+ of CD45RO+ Tregs
% CXCR5+ of CD45RO+ Tregs In one embodiment, the cells of the responder and non responder are obtained from peripheral blood. The cells may be enriched for a leukocyte subset. For example, the cells may be enriched for mononuclear or polynuclear cells.

The assessment of the cells of a positive responder who has been selected for formation of a positive response control may be performed by mass cytometry methods including TOFcytometry, according to the methodology described below for assessment of cells of the test sample.

Determining Distribution of Cells in Test Sample

The distribution of cells in the test sample may be determined according to the following steps:
 a. assessing each cell of the test sample for the expression of each biomarker of the group of biomarkers of the positive response control;
 b. classifying each cell of the test sample into one of the series of classes of the positive response control;
 c. measuring the number of cells of the test sample in each class of the series of classes of the positive response control.

An assessment of the distribution of cells in the test sample is a consideration of the relative number of cells within each class of the series of classes of the positive response control. This may also be expressed as the number of cells per class as a % of total number of cells of the test sample. These assessments may be completed by mass cytometry methods including TOFcytometry, which enables individual cell assessment for expression of a large number of biomarkers (40 or more) per cell See: [Spitzer M H and G P Nolan 2016 *Cell* 165: 780-791].

Comparing Test Sample and Positive Response Control

The determination of whether the distribution of the cells of the test sample within the series of classes of the positive response control is the same as the distribution of cells described by the positive response control generally requires a step of:
 a. comparing the measured number of cells of the test sample in each class of the series of classes of the positive response control with the number of cells of the positive response control in each class of the series of classes of the positive response control;
  This step can be performed in silico using available software packages.

Disease and Conditions

The invention is particularly applicable to disease or conditions associated with a loss of control of cell division, and in particular, those pathologies characterised by abnormal cell proliferation leading to formation of differentiated or undifferentiated cells. In one embodiment the condition is a hyperplastic condition. In another embodiment, the condition is a neoplastic condition. The condition may be a benign or malignant tumour, and the tumour may be primary or metastatic. In a particularly preferred embodiment, the condition is cancer in the form of melanoma, squamous and non squamous non-small cell lung cancer, mesothelioma, head and neck cancer, bladder cancer, Hodgkin's lymphoma, renal cell carcinoma and urothelial carcinoma.

Immunomodulatory Agents

In a particularly preferred embodiment, the immunomodulatory agent is a check-point inhibitor.

Immune check-points are generally understood as molecules that regulate the immune system by either stimulating or dampening the immune response to antigen. Of particular relevance are checkpoint molecules that dampen the immune system (examples including PD-1 and CTLA-4) and for the purpose of the methods described herein, molecules that inhibit the dampening of the immune system by checkpoint molecules. Such 'check-point inhibitors' may be antibodies, peptides or other small molecules.

According to the invention, the check-point inhibitor is preferably an inhibitor of CTLA-4 or an inhibitor of PD-1. Other examples of check-point inhibitors include inhibitors of A2AR, CD276 (B7-H3), VTCN1 (B7-H4), IDO (Indoleamine 2,3-dioxygenase), KIR (killer—cell immunoglobulin-like receptor), LAG 3 (lymphocyte activation gene-3), TIM-3 (T-cell immunoglobulin domain and mucin domain 3) and VISTA (V-domain Ig suppressor of T cell activation). Preferably the inhibitor is an inhibitor of the binding interaction of CTLA-4 with its ligand, or PD-1 with its ligand. Preferably the checkpoint inhibitor is an anti—CTLA-4 antibody or an anti-PD-1 antibody. In one embodiment, the check-point inhibitor is ipilimumab, pembrolizumab or nivolumab.

In one embodiment, the method may include the further step of administering the immunomodulatory agent to the individual for whom the likelihood of formation of a clinical response is to be determined where a higher likelihood of formation of a clinical response is determined for the individual.

In one embodiment, there is provided a composition for determining the likelihood of the formation of a clinical response to an immunomodulatory agent, the composition comprising at least 9, typically at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40, antibodies, each antibody specific for a biomarker selected from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10. In one embodiment, each antibody specific for a biomarker is labelled with a moiety that is unique to an antibody that binds that biomarker. In one embodiment, the moiety is a metal isotope or fluorochrome. In one embodiment, the antibody is a monoclonal antibody.

In one embodiment, there is provided a kit for determining the likelihood of the formation of a clinical response to an immunomodulatory agent, the kit comprising at least 9, typically at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40, antibodies, each antibody specific for a biomarker selected from the group consisting of CD45, CD45RA, CD45RO, CD3, CD4, CD8, CD19, CD20, CD14, CD16, CD11b, CD11c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10. In one embodiment, each antibody specific for a biomarker is labelled with a moiety that is unique to an antibody that binds that biomarker. In one embodiment, the moiety is a metal isotope or fluorochrome. In one embodiment, the antibody is a monoclonal antibody.

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1

Determining Distribution of Cells within a Sample

A peripheral blood sample is obtained using venepuncture, with the blood collected into a tube that prevents clotting (for example, one containing EDTA or heparin). The leucocytes are then prepared immediately for cytometry, or cryopreserved for long-term storage, for example at −80 or in liquid nitrogen. Cryopreserved leucocytes are thawed before analysis using conventional techniques.

The distribution of cells is determined using a technique that identifies expression of pre-determined proteins or transcripts within each single cell within the sample. Typically, the cells are treated with a mixture of between 10 and 40 antibodies, each specific for an individual cell protein and labelled with a unique metal isotope or fluorochrome such that the treated sample can be analysed using mass cytometry or fluorescence cytometry, respectively.

In the example provided, the cells are treated with a mixture of metal-labelled monoclonal antibodies that detect the following proteins:

CD45
CD45RA
CD45RO
CD3
CD4
CD8
CD19
CD20
CD14
CD16
CD11b
CD11c
CD66b
CD304
FoxP3
CD127
CD25
CD56
HLA-DR
IgD
CD27
CD86
FCRL3
CD274 (PD-1)
CD279 (PD-L1)
TIGIT
CD38
Ki67
Granzyme B
CD134 (OX40)
CD194 (CCR4)
CD195 (CCR5)
CD196 (CCR6)
CD197 (CCR7)
Integrin beta7
CLA
CD183 (CXCR3)
CD185 (CXCR5)
CCR10.

The metal isotopic data from each single cell within the sample is collected using a mass cytometer such as the Helios and the resulting data file is analysed in order to calculate the number and percentage of cells within subsets of the major circulating cell populations, including T cells, B cells, NK cells, monocytes, dendritic cells. This process, here termed 'gating' determines the number of cells that fall within certain categories defined on the basis of expression of the proteins (here termed 'markers') detected by the metal-labelled antibodies.

After gating, the % representation of the populations is determined. Table 1 above describes an exemplary list of populations that can be gated according to the monoclonal antibodies used in this example.

Example 2

Comparing the Distribution of Cell Populations in Different Individuals

This can be achieved by many statistical techniques, including machine learning. A technique based on microarray analysis is demonstrated here.

The % data of all the individuals to be compared is loaded into a microarray analysis software package such as MeV. Row normalisation is performed so that the relative weight of each cell population within the dataset is equal to that of every other population.

Graphical output after row normalisation is shown in FIG. 1.

Example 3

Distinguishing Responders from Non-Responders in a Dataset from Stage III-IV Patients Treated with Anti-PD-1 Therapy Patients who were about to start anti-PD-1 therapy for advanced melanoma provided a blood sample from which peripheral blood mononuclear cells were separated using a Ficoll-Hypaque gradient and cryopreserved in liquid nitrogen. A second blood sample was taken just prior to administration of the second dose of anti-PD-1 therapy (either 2 or 3 weeks after the first dose). Cells were thawed and prepared for mass cytometric analysis in batches that included the paired patient samples and a single sample from an age and sex-matched healthy control individual. Mass cytometry used the antibody mixture described above.

Patients were assigned to responder and non-responder groups according to the RECIST 1.0 criteria—the responder group included patients classified as complete response, partial response and stable disease, while the non-responder group consisted of those who had progressive disease.

In our initial analysis of 20 patients, the 7 non-responder patients had a significantly different distribution of cell subsets before therapy, compared with responder patients and with age and sex matched controls. The parameters that were significantly different between responders and non-responders did not change significantly after anti-PD-1 therapy (FIG. 2).

Because all the non-responders in our initial study were male, we checked carefully that differences between males and females were not responsible for the signature. In a paired analysis, in which the pre-therapy sample from each male patient (7 non-responders, 5 responders and 1 adverse event) was compared with its age-matched male control, a strong signature was still clearly present (FIG. 3).

Figure 2:
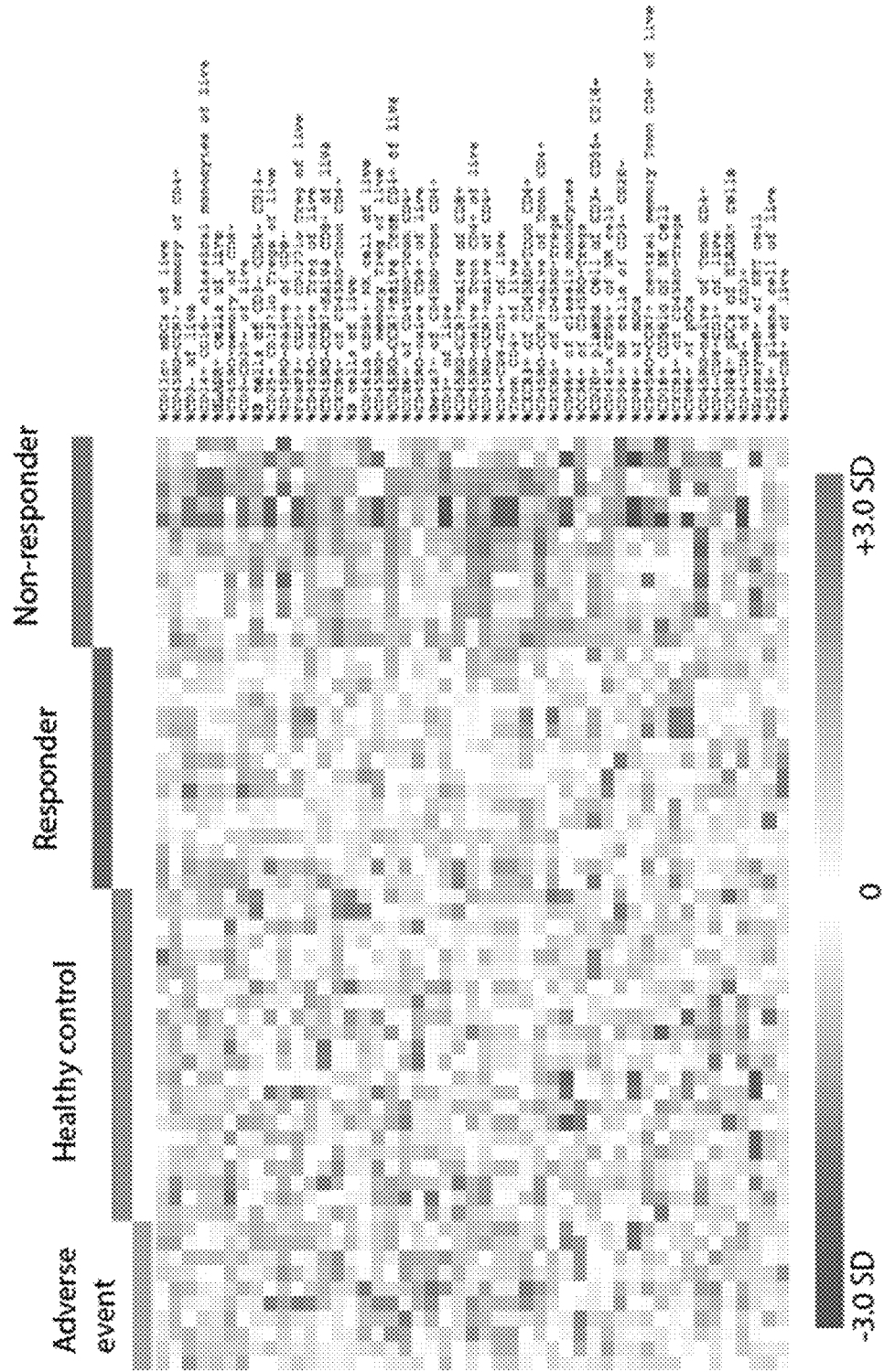
FIG. 2. Cell subsets that were significantly different between advanced melanoma patients who were non-responders versus responders to anti-PD-1 therapy, as determined using Significance Analysis of Microarrays (SAM). Columns show paired pre- and post-therapy samples from each patient (7 responders, 6 non-responders and 5 patients who discontinued therapy due to adverse events). Age- and sex-matched controls provided a single sample.
Figure 3:
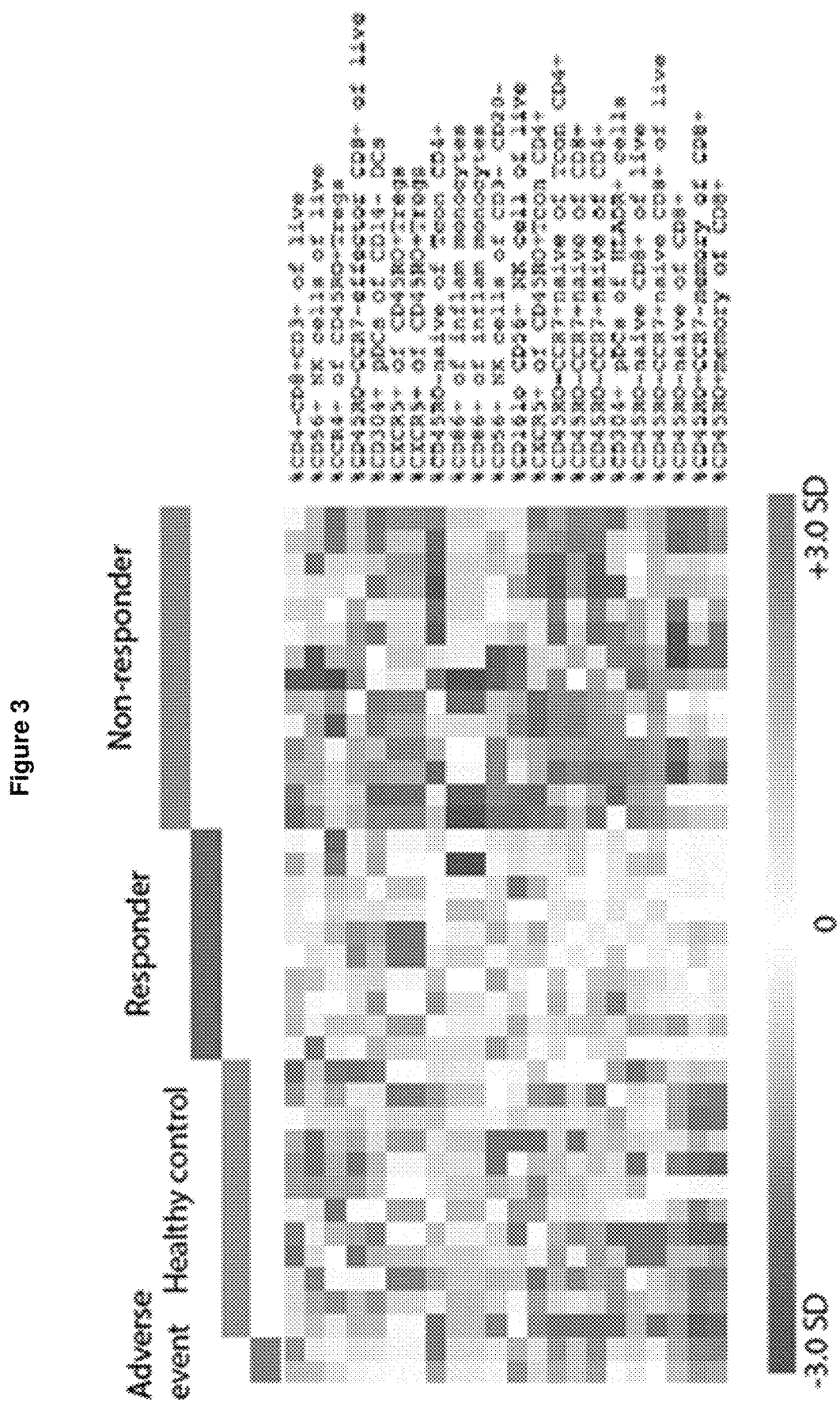
FIG. 3. Cell subsets that were significantly different in a pairwise analysis between pre-therapy samples from male patients and age-matched controls.

The differences between the individual signatures in FIGS. 2 and 3 are due to the small subject numbers. However either statistical analysis could be used to distinguish between responders and non-responders.

Example 4

Application of the Invention to a Sample from a Cancer Patient in Order to Predict Response to Therapy The patient's leucocytes will be exposed to a standardised antibody mixture that has previously been shown to allow a distinction to be made between responder and non-responder groups (as exemplified above). Mass cytometric analysis will be performed with appropriate controls (for example, samples from additional patients and age and sex matched healthy subjects). The distribution of cell populations within the patient sample will be compared with the distribution from samples analysed in the same batch, and with the historical dataset (such as that illustrated in FIGS. 2& 3). Statistical techniques will be applied to estimate the probability that the sample comes from the responder or non-responder group. These techniques may include machine learning techniques.

The number of samples within the comparison dataset of responder and non-responder patients will depend on the magnitude of the differences in cell distribution between responder and non-responder patients with a particular cancer being treated with a particular therapy. In the illustrated example of advanced melanoma patients treated with anti-PD-1 therapy, 20 patients were sufficient.

Example 5

Distinguishing Responders from Non-Responders in a Dataset from Non-Small-Cell Lung Cancer Patients Treated with Anti-PD-1 Therapy Patients who were about to start anti-PD-1 therapy for non-small-cell lung cancer provided a blood sample from which peripheral blood mononuclear cells were separated using a Ficoll-Hypaque gradient and cryopreserved in liquid nitrogen. A second blood sample was taken just prior to administration of the second dose of anti-PD-1 therapy (either 2 or 3 weeks after the first dose). Cells were thawed and prepared for mass cytometric analysis in batches that included one of both of the paired patient samples and a single sample from an age and sex-matched healthy control individual. Mass cytometry used the antibody mixture described above.

Patients were assigned to responder and non-responder groups according to the RECIST 1.0 criteria—the responder group included patients classified as complete response, partial response and stable disease, while the non-responder group consisted of those who had progressive disease.

Figure 4:
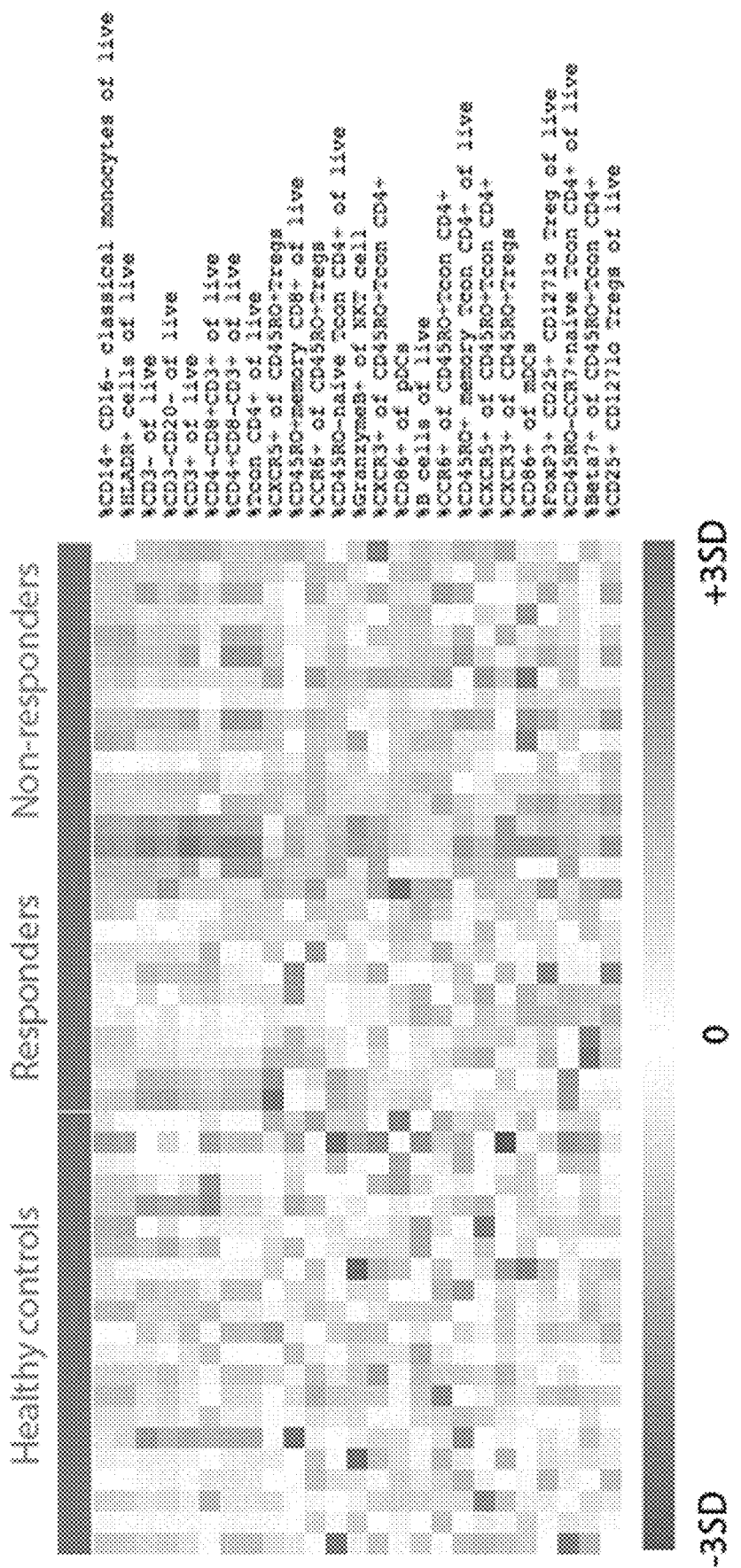
FIG. 4. Cell subsets that were significantly different between non-small cell lung cancer patients who were non-responders versus responders to anti-PD-1 therapy, as determined using Significance Analysis of Microarrays (SAM).

In our initial group of 20 patients, the 12 non-responder patients had a significantly different distribution of subsets before therapy, compared with responder patients and with age and sex matched controls. The parameters that were significantly different between responders and non-responders did not change significantly after anti-PD-1 therapy (FIG. 4).

Comparison with the signature in advanced melanoma (FIG. 2) indicated that a majority of the subsets making up the signature were shared, including those that define CD4 T cell, Treg, B cell, monocyte and DC subsets. Those defining NK and CD8 subsets were not shared, indicating that these may differ between melanoma and non-small-cell lung cancer.

Example 6

Generation of a Minimal Response Signature Using Machine Learning

Figure 5:
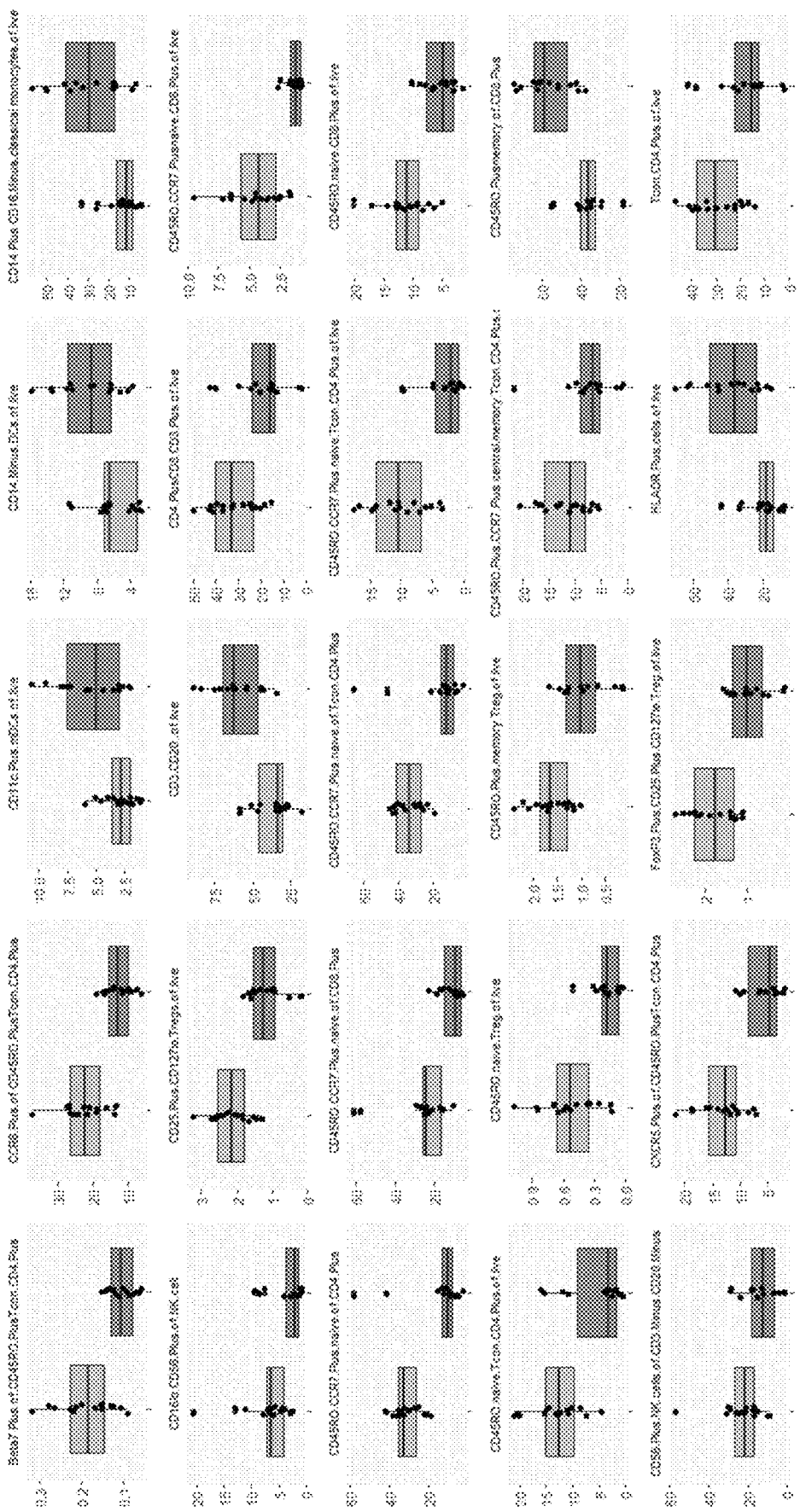
FIG. 5. Box plots of the 25 parameters selected by SVM in the analysis of the advanced melanoma dataset illustrated in FIG. 1. Boxes indicate the interquartile range with the median indicated by the central line. Individual values are indicated by the filled black circles.

Machine learning techniques (support vector machine (SVM) analysis) were applied to the dataset illustrated in FIG. 1. Parameter reduction generated 25 parameters providing the best discrimination between the responder and non-responder patients. FIG. 5 shows box plots of the comparison between responders and non-responders for the 25 parameters.

Prediction errors for the 25 individual parameters ranged from 0.13 to 0.61. For random pairs of parameters, prediction errors ranged from 0.03 to 0.59. For random triplets of parameters, prediction errors ranged from 0 to 0.54. The 14 triplets that gave prediction errors of 0 are shown in FIG. 6.

Example 7

A Conventional Flow Panel can Predict Clinical Response to Anti-PD-1 Therapy in Advanced Melanoma Patients The analysis shown in FIG. 6 indicated that it would be possible to predict whether advanced melanoma patients would respond to anti-PD-1 therapy using only 12 subsets, which could be achieved with a more limited panel of markers than those used in the initial mass cytometric analysis. Specifically, we designed a conventional 13 parameter fluorescence-based flow cytometry panel using monoclonal antibodies to 10 surface markers plus forward and side scatter and a fixable live-dead dye. The panel consisted of monoclonal antibodies reactive with CD4, CD8, CD25, CD127, CD45RO, CD62L, CD196 (CCR6), Integrin beta7, CD16 and CD56. A blinded set of samples consisting of 5 responder and 5 non-responder samples were analysed on a 5 laser flow cytometer and the data analysed to enumerate all the possible subsets identified by the panel.

Figure 7:
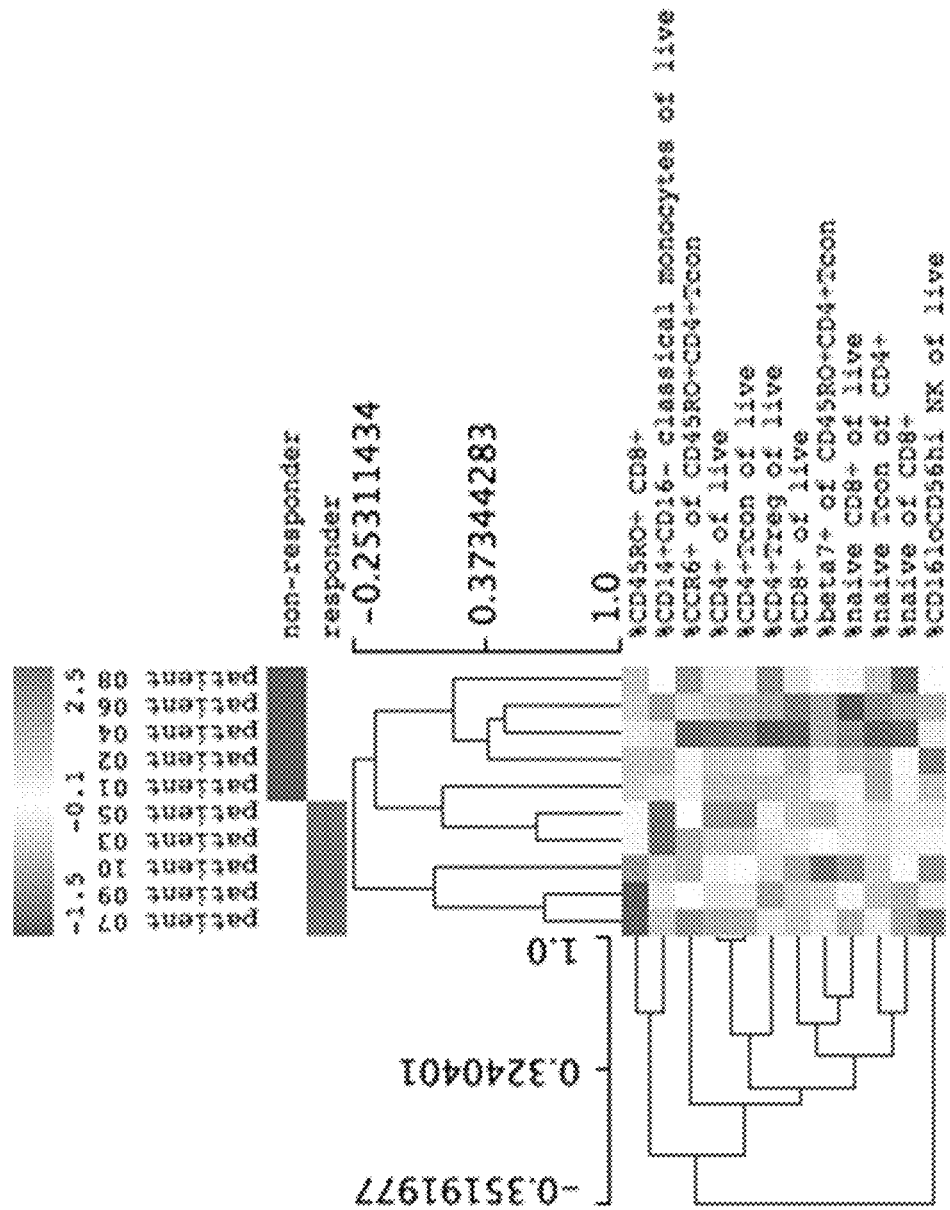
FIG. 7. Fluorescence flow cytometric analysis of blinded samples from advanced melanoma patients. Unsupervised clustering segregated pre-treatment blood samples from melanoma patients who did or did not respond to anti-PD-1 therapy. Samples were stained with a 10-colour fluorescently labelled antibody panel that identified all the individual subsets indicated in FIG. 6.

An unsupervised clustering analysis of the data from the 10 samples, using a combination of the subsets indicated in FIG. 6 is shown in FIG. 7. After data analysis was completed, the samples were unblended to reveal that the samples from responder and non responder patients clustered together (FIG. 7).

Example 8

Prediction of Clinical Response to Nivolumab and Pembrolizumab in Advanced Melanoma Patients In the examples described above, response prediction was equally effective for the two most commonly used anti-PD-1 agents, nivolumab and pembrolizumab.

The distribution of the advanced melanoma patients between the 2 agents was as follows:

|  | nivolumab | pembrolizumab |
|---|---|---|
| responder | 3 | 5 |
| non-responder | 1 | 6 |

Example 9

Figure 8:
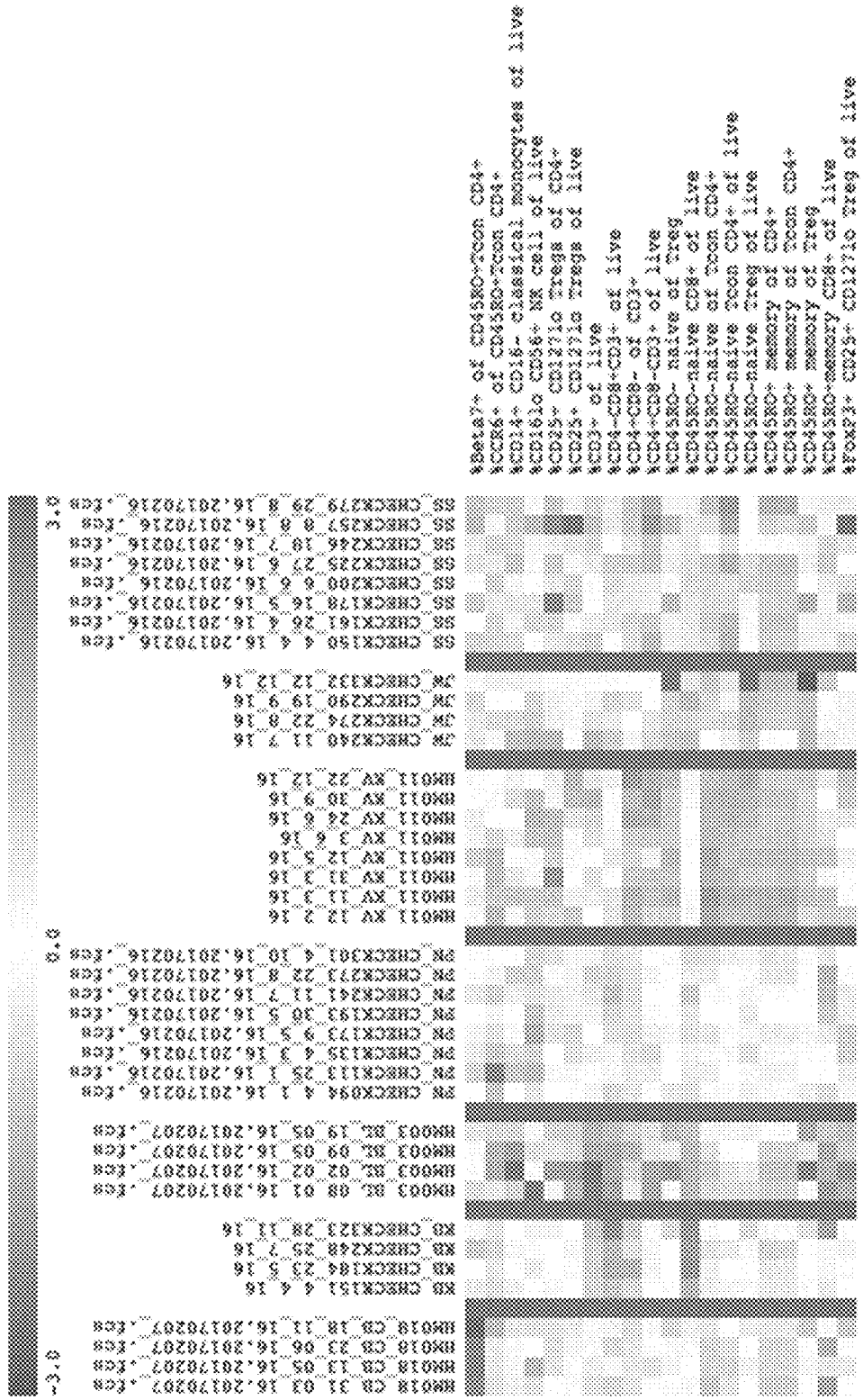
FIG. 8. Longitudinal series from 7 advanced melanoma patients on treatment with anti-PD-1, showing stability of the immune signature over periods of up to 10 months (dates in dd_mm_yy format are indicated after the sample names in the column labels).

Predictive Signatures are Stable Through Time and Multiple Courses of Anti-PD1 Therapy Analysis of longitudinal series of samples from multiple advanced melanoma patients indicated that the predictive signatures are stable for at least 10 months (FIG. 8).

The invention claimed is:

1. A method for determining the likelihood of the formation of a clinical response in an individual to therapy with a checkpoint inhibitor for treatment of cancer of the individual, including:
  (i) providing a positive response control from a positive responder, or a plurality of positive responders, each positive responder in the form of an individual who has formed the clinical response to therapy with the checkpoint inhibitor for treatment of the cancer, the positive response control describing the distribution of cells of a blood sample of the positive responder within a series of classes, the distribution according to the expression by each cell of the sample of a group of biomarkers so that cells having the same expression of biomarkers of the group are classified in the same class;
  (ii) determining the distribution of cells of a test sample within the series of classes of the positive response control, the test sample in the form of a sample of cells from blood of the individual for the whom the likelihood of formation of a clinical response is to be determined; and
  (iii) determining whether the distribution of the cells of the test sample within the series of classes of the positive response control is the same as the distribution of cells described by the positive response control;
  wherein the group of biomarkers includes a CD4 or CD8 T cell marker, and/or a B cell or plasma cell marker and/or a NK cell marker and/or a monocyte or dendritic cell marker, and at least 9 markers selected from the group consisting of CD45, CD45RA, CD45RO, CD3, CD4, CD8, CD19, CD20, CD14, CD16, CD11 b, CD11 c, CD66b, CD304, FoxP3, CD127, CD25, CD56, HLA-DR, IgD, CD27, CD86, FCRL3, CD274 (PD-1), CD279 (PD-L1), TIGIT, CD38, Ki67, Granzyme B, CD134 (OX40), CD194 (CCR4), CD195 (CCR5), CD196 (CCR6), CD197 (CCR7), Integrin beta7, CLA, CD183 (CXCR3), CD185, (CXCR5) and CCR10,
  wherein the series of classes comprises:
  CD45RO$^-$, CCR7$^-$, naïve of CD4$^+$;
  FoxP3$^+$, CD25$^+$, CD127$^{lo}$, T$_{reg}$ of live;
  CD45RO$^+$, memory T$_{reg}$ of live;
  CD45RO$^-$ CCR7$^+$ naïve CD4$^+$ Tcon of live;
  CD45RO$^+$ CCR7$^+$ central memory CD4$^+$ Tcon of live;
  Integrin beta 7$^+$ of CD45RO$^+$ Tcon CD4$^+$;
  CCR6$^+$ of CD45RO$^+$ Tcon CD4$^+$;
  CD45RO$^-$ naïve CD8$^+$ of live;
  CD45RO$^-$ CCR7$^+$ naïve CD8$^+$ of live;
  CD45RO$^+$ memory of CD8$^+$;
  CD56$^+$ NK cells of CD3$^-$CD20$^-$; and
  CD14$^+$CD16$^-$ classical monocytes of live;
  or
  CD45RO+CD8$^+$;
  CD14$^+$, CD16$^-$, classical monocytes of live;
  CCR6$^+$ of CD45RO$^+$ Tcon CD4$^+$ Tcon;
  CD4$^+$ of live;
  CD4$^+$ Tcon of live;
  CD4$^+$T$_{reg}$ of live;
  CD8$^+$ of live;
  Integrin beta 7$^+$ of CD45RO$^+$ Tcon CD4$^+$;
  Naïve CD8$^+$ of live;
  Naïve Tcon of CD4$^+$;
  Naïve of CD8$^+$; and
  CD16$^{lo}$ CD56$^{hi}$, NK of live,
  and wherein the checkpoint inhibitor is an antibody which is an inhibitor of the binding interaction between PD-1 and PD-L1, whereby a higher likelihood of formation of a clinical response is determined where the distribution of the cells of the test sample within the series of classes of the positive response control is the same as the distribution of cells described by the positive response control and whereby a lower likelihood of formation of a clinical response is determined where the distribution of the cells of the test sample within the series of classes of the positive response control is not the same as the distribution of cells described by the positive response control, and administering the checkpoint inhibitor to the individual where a higher likelihood of formation of a clinical response is determined for the individual.

2. The method of claim 1, wherein (ii) determining the distribution of cells of a test sample within the series of classes of the positive response control comprises the steps of:
   a. assessing each cell of the test sample for the expression of each biomarker of the group of biomarkers of the positive response control;
   b. classifying each cell of the test sample into one of the series of classes of the positive response control;
   c. measuring the number of cells of the test sample in each class of the series of classes of the positive response control;
      thereby determining the distribution of cells of the test sample within the series of classes of the positive response control.

3. The method of claim 2, wherein (iii) determining whether the distribution of the cells of the test sample within the series of classes of the positive response control is the same as the distribution of cells described by the positive response control comprises the step of:
   comparing the measured number of cells of the test sample in each class of the series of classes of the positive response control with the number of cells of the positive response control in each class of the series of classes of the positive response control;
   thereby determining whether the distribution of the cells of the test sample within the series of classes of the positive response control is the same as the distribution of cells described by the positive response control.

4. The method of claim 1, wherein the positive response control is from a plurality of positive responders.

5. The method of claim 1, wherein the positive response control is from a positive responder or a plurality of positive responders that has formed a complete response or a partial response.

6. The method of claim 1, wherein the positive response control describes the distribution of cells in terms of the number of cells within each class as a percentage of total number of cells of the sample.

7. The method of claim 1, wherein the positive response control describes the distribution of cells of a sample of a positive responder prior to therapy, or post therapy, of the positive responder with the checkpoint inhibitor.

8. The method of claim 1, wherein the cancer is selected from the group consisting of melanoma, squamous non-small cell lung cancer, non squamous non-small cell lung cancer, mesothelioma, head and neck cancer, bladder cancer, Hodgkin's lymphoma, renal cell carcinoma, and urothelial carcinoma.

9. The method of claim 1, wherein the checkpoint inhibitor is an anti-PD-1 antibody.

10. The method of claim 9, wherein the anti-PD-1 antibody is pembrolizumab or nivolumab.

11. The method of claim 1, wherein the positive response control is identified by a method comprising the following steps
   (i) providing a responder cell sample or a plurality of responder cell samples, each responder cell sample in the form of blood cells of an individual who has responded to immune checkpoint inhibitor therapy;
   (ii) providing a non responder cell sample or a plurality of non responder cell sample, each non responder cell sample in the form of blood cells of an individual who has not responded to immune checkpoint inhibitor therapy;
   (iii) applying a cell distribution analysis to the responder cell sample(s) whereby the cells in the responder cell sample(s) are distributed within a series of classes according to the expression by each cell of a group of biomarkers so that cells having the same expression of each biomarker of the group are classified in the same class, thereby forming a responder cell distribution profile;
   (iv) applying the cell distribution analysis to the non responder cell sample(s), thereby forming a non responder cell distribution profile;
   (v) identifying a distribution of cells in the responder cell distribution profile that is not seen in the non responder cell distribution profile,
      wherein a distribution of cells in the responder cell distribution profile that is not seen in the non responder cell distribution profile is identified as a positive response control.

12. The method of claim 11, wherein the responder cell distribution profile is from applying the cell distribution analysis to a plurality of responder cell samples.

13. The method of claim 12, wherein the plurality of responder cell samples is from a plurality of individuals who have responded to immune checkpoint inhibitor therapy.

14. The method of claim 11, wherein the non responder cell distribution profile is from applying the cell distribution analysis to a plurality of non responder cell samples.

15. The method of claim 14, wherein the plurality of non responder cell samples is from a plurality of individuals who have not responded to immune check point inhibitor therapy.

16. The method of claim 1, wherein the series of classes comprises:
   $CD45RO^-$, $CCR7^-$, naïve of $CD4^+$;
   $FoxP3^+$, $CD25^+$, CD127lo, Treg of live;
   $CD45RO^+$ memory T reg;
   $CD45RO^-$ $CCR7^+$ naïve $CD4^+$ Tcon of live;
   $CD45RO^+$ $CCR7^+$ central memory $CD4^+$ Tcon of live;
   Integrin beta $7^+$ of $CD45RO^+$ Tcon $CD4^+$;
   $CCR6^+$ of $CD45RO^+$ Tcon $CD4^+$;
   $CD45RO^-$ naïve $CD8^+$ of live;
   $CD45RO^-$ $CCR7^+$ naïve $CD8^+$ of live;
   $CD45RO^+$ memory of $CD8^+$;
   $CD56^+$ NK cells of $CD3^-CD20^-$; and
   $CD14^+CD16^-$ classical monocytes.

17. The method of claim 1, wherein the series of classes comprises:
   $CD45RO+Cd8^+$;
   $CD14^+$, $CD16^-$, classical monocytes of live;
   $CCR6^+$ of $CD45RO^+$ Tcon $CD4^+$;
   $CD4^+$ of live;
   $CD4^+$ Tcon of live;
   $CD4^+$ Treg of live;
   $CD8^+$ of live;

Integrin beta 7$^+$ of CD45RO$^+$ Tcon CD4$^+$;
Naïve CD8$^+$ of live;
Naïve Tcon of CD4$^+$;
Naïve of CD8$^+$; and
CD16$^{lo}$ CD56$^h$, NK of live.

* * * * *